United States Patent
Dust

(10) Patent No.: US 6,843,129 B2
(45) Date of Patent: Jan. 18, 2005

(54) ULTRASOUND MEASUREMENT OF THE THICKNESS OF A WEAKLY REFLECTIVE SUBLAYER BY ECHO PERIOD SUMMATION

(75) Inventor: Martin Dust, Erlangen (DE)

(73) Assignee: Framatome ANP GmbH, Erlangen (DE)

( * ) Notice: Subject to any disclaimer, the term of this patent is extended or adjusted under 35 U.S.C. 154(b) by 0 days.

(21) Appl. No.: 10/673,967

(22) Filed: Sep. 29, 2003

(65) Prior Publication Data

US 2004/0074305 A1 Apr. 22, 2004

Related U.S. Application Data

(63) Continuation of application No. PCT/EP02/02236, filed on Mar. 1, 2002.

(30) Foreign Application Priority Data

Mar. 28, 2001 (DE) .......................................... 101 15 329

(51) Int. Cl.⁷ .............................................. G01N 29/20
(52) U.S. Cl. .............................. 73/597; 73/602; 73/614; 73/627
(58) Field of Search .......................... 73/597, 599, 600, 73/602, 614, 622, 625, 627; 376/252

(56) References Cited

U.S. PATENT DOCUMENTS

| | | | |
|---|---|---|---|
| 4,865,040 A | * 9/1989 | Ogasawara | 600/450 |
| 4,875,372 A | 10/1989 | Gilbert | 73/614 |
| 4,918,989 A | 4/1990 | Desruelles et al. | 73/627 |
| 4,991,440 A | 2/1991 | Pleinis et al. | 73/615 |
| 5,038,615 A | 8/1991 | Trulson et al. | 73/597 |
| 5,063,780 A | * 11/1991 | Landry et al. | 73/622 |
| 5,201,225 A | * 4/1993 | Takahashi et al. | 73/615 |
| 5,349,860 A | * 9/1994 | Nakano et al. | 73/597 |
| 5,418,823 A | * 5/1995 | Kervinen et al. | 376/245 |
| 5,577,088 A | * 11/1996 | Senevat et al. | 376/252 |
| 5,608,165 A | * 3/1997 | Mozurkewich, Jr. | 73/599 |
| 5,635,644 A | * 6/1997 | Ishikawa et al. | 73/614 |
| 5,661,241 A | * 8/1997 | Harth et al. | 73/622 |
| 6,035,717 A | * 3/2000 | Carodiskey | 73/597 |

FOREIGN PATENT DOCUMENTS

DE 41 02 576 A1 8/1991

OTHER PUBLICATIONS

Munroe, D.M. (edited by Sydenham, P. H.): "Signal-to-Noise Ration Improvement", Handbook of Measurement Science, John Wiley & Sons, Ltd., vol. 1, 1982, pp. 431–433.

* cited by examiner

Primary Examiner—Hezron Williams
Assistant Examiner—Jacques M. Saint-Surin
(74) Attorney, Agent, or Firm—Laurence A. Greenberg; Werner H. Stemer; Gregory L. Mayback

(57) ABSTRACT

An ultra sonic sound measurement is used to determine the thickness of a partial layer in a multi-layered structure with reduced boundary surface reflections. A plurality of transmission pulses are produced on a predetermined point on the structure with the help of an ultra sonic probe head. The resulting echo signals associated with a transmission pulse are recorded digitally as an HP image. A plurality of wall thickness echo periods from different running periods are superimposed in a homologous manner with the aid of a computer program.

2 Claims, 5 Drawing Sheets

ULTRASOUND MEASUREMENT OF THE THICKNESS OF A WEAKLY REFLECTIVE SUBLAYER BY ECHO PERIOD SUMMATION

CROSS-REFERENCE TO RELATED APPLICATION

This application is a continuation of copending International Application No. PCT/EP02/02236, filed Mar. 1, 2002, which designated the United States and was not published in English.

BACKGROUND OF THE INVENTION

FIELD OF THE INVENTION

The invention relates to an ultrasound method for measuring the thickness of weakly reflective sublayers of a multilayer component. In such a component, the various layers are formed of materials with similar acoustic impedances. Only an extremely small proportion, namely approximately 1%, of an acoustic impulse that is generated by an ultrasound probe is thus reflected at the interface between the materials. Accordingly, the reflected interface echo has amplitudes in the range of the amplitudes of conventional noise signals, for instance noise signals that are brought about by incomplete damping of the ultrasound head or by transversal wave echoes. Therefore, in measuring operations according to the prior art, the achievable signal/noise ratio is frequently insufficient for unambiguously identifying the boundary layer echo.

U.S. Pat. No. 4,918,989 describes an ultrasound method for measuring the thickness of a liner layer of a cladding tube for nuclear fuel wherein the signal/noise ratio is increased by exploiting the superposition of two multiply reflected echo pulses with different reflection behavior or beam paths but with identical transit times. The emerging signal should thus be stronger and should contrast more clearly from noise signals compared to an echo pulse that is reflected once at the interface between the liner layer and the tube material. The multiple reflections only become important for later wall thickness echoes, where disturbances based on transversal waves are great, and where the useful echoes are small owing to longer transit paths. The improvement of the signal/noise ratios is thus small.

Published, Non-Prosecuted German Patent Application DE 41 02 576 A1, corresponding to U.S. Pat. No. 4,991,440, describes another ultrasound method for determining the thickness of an inner layer of a cladding tube for nuclear fuel. Time gates which filter out the noise signals before and after the interface echo are employed for purposes of bringing the signal that is reflected at the interface between the inner layer and the cladding tube more prominently into the foreground relative to noise signals. But disturbances near the boundary layer echo remain untouched.

SUMMARY OF THE INVENTION

It is accordingly an object of the invention to provide a ultrasound measurement of the thickness of a weakly reflective sublayer by echo period summation that overcomes the above-mentioned disadvantages of the prior art methods of this general type, with which the signal/noise ratio can be improved in the thickness determination on sublayers with weak reflection.

With the foregoing and other objects in view there is provided, in accordance with the invention, a method for ultrasound measurement of a sublayer thickness of a multilayer component with low interface reflection. The method includes generating a plurality of transmission impulses at a predetermined location of the multilayer component using an ultrasound probe, digitally recording, as an HF image, resulting echo signals associated with a transmission impulse, and homologously superimposing a plurality of wall thickness echo periods of different transit times using a computer program.

Accordingly, multiple transmission pulses are generated at a predetermined location of a multilayer component by an ultrasound probe, and the echo pulses that are allocated to a transmission pulse are digitally recorded as an HF image.

After being averaged for purposes of suppressing the electronic noise, the HF image is then processed by a computer program so as to homologously superimpose a plurality of echo periods, each of which is defined by two chronologically consecutive back-wall echoes between which noise signals are embedded. The invention is based on the observation that the time sequence of the noise signals of the individual echo periods varies extensively, whereas the interface echoes exhibit a constant periodicity. Owing to their strict periodicity, the interface echoes become stronger than the noise signals with the superposition of a plurality of echo periods. As a result of the superposition, the interface echo clearly contrasts with the noise signals in the digital recording and is consequently easier to identify and evaluate. The inventive method can be applied with particular advantage in determining the thickness of a liner layer of cladding tubes for nuclear fuel.

Other features which are considered as characteristic for the invention are set forth in the appended claims.

Although the invention is illustrated and described herein as embodied in a ultrasound measurement of the thickness of a weakly reflective sublayer by echo period summation, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
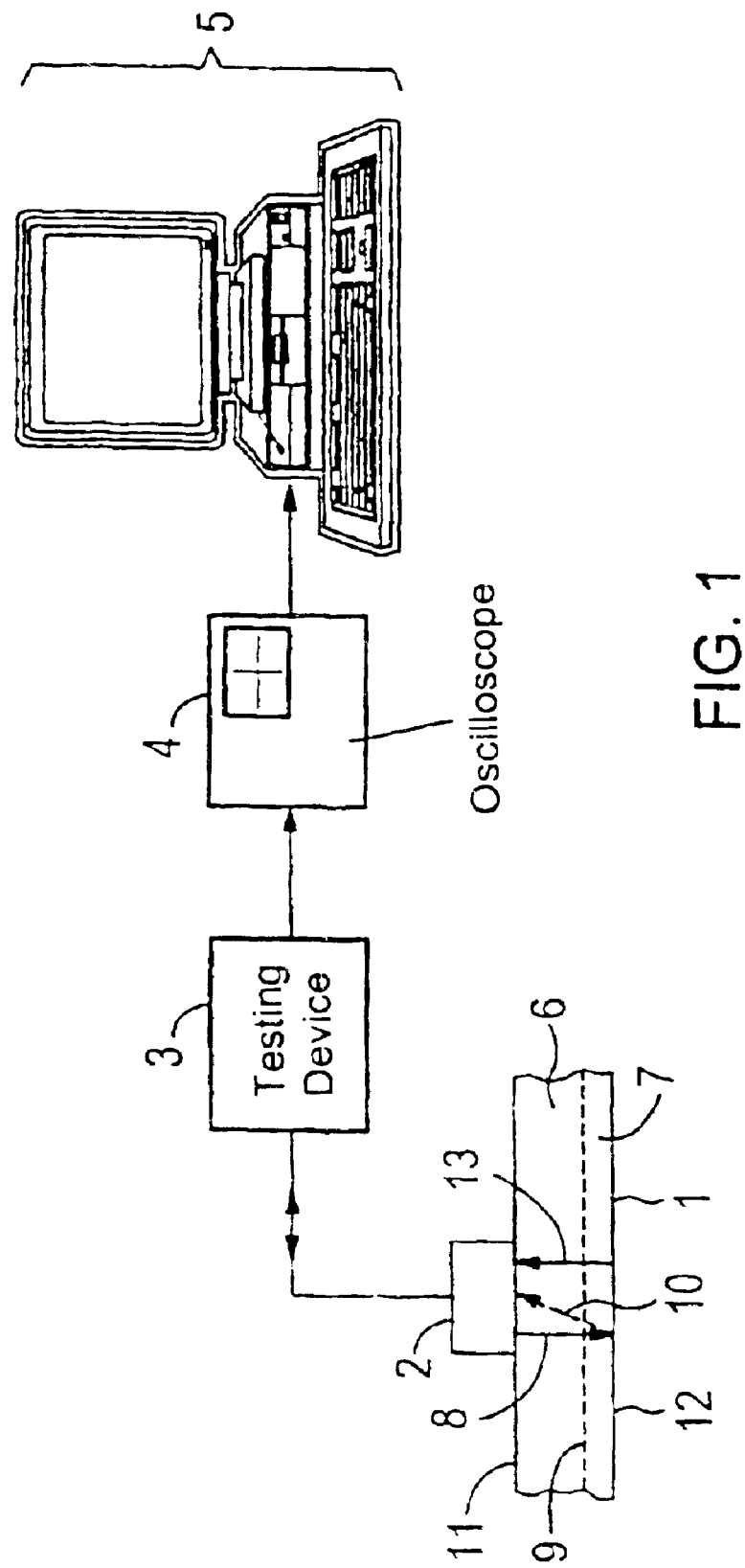
FIG. 1 is a schematic representation of a device for carrying out a measuring method on a two-layer component according to the invention.

Referring now to the figures of the drawing in detail and first, particularly, to FIG. 1 thereof, there is shown a schematic representation of a typical structure for ultrasound measurement of a component 1. An ultrasound probe or transceiver 2 is disposed at a surface of the component 1. An acoustic coupling is achieved by a contacting technique with or without a start-up length. The echo signals that are received by the ultrasound probe 2 are picked up by an ultrasound testing device 3 and recorded by a digital oscilloscope 4, for instance in the form of an HF image. A data processing system such as a personal computer 5 for processing the data of the HF image is connected to the oscilloscope 4.

Figure 2:
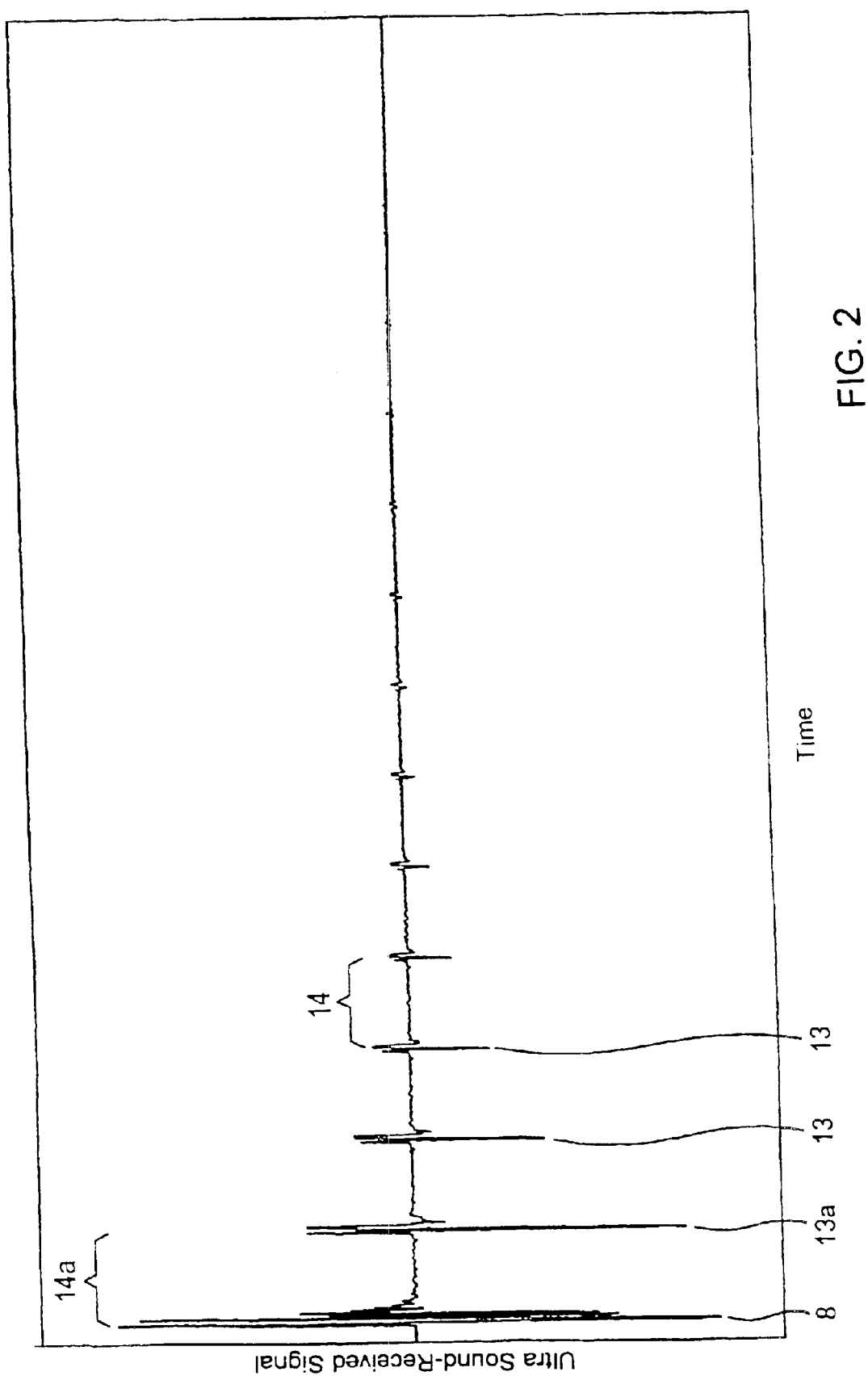
FIG. 2 is a HF image of an ultrasound measurement that was performed at a predetermined location of the component.

The component 1 is composed of two layers 6, 7 that are formed of very similar materials with respect to acoustic impedance. The greater part of a transmission pulse 8 which is generated by the probe 2 thus penetrates an interface 9 between the two layers 6, 7. Only a portion of at most 1 rel.% is reflected at the interface 9 and received by the probe 2 as a weak interface echo 10. On the other hand, a back-wall echo 13 that is reflected by a back wall 12 of the component 2 is substantially stronger. If the interface has a reflection factor of 0.01, for example, the back-wall echo 13 is 99 times stronger than the interface echo 10. The latter is therefore no longer detectable in an HF image with low amplification (see FIG. 2). However, the image according to FIG. 2 can serve for determining the wall thickness based on the time interval between two consecutive back-wall echoes 13.

Figure 3:
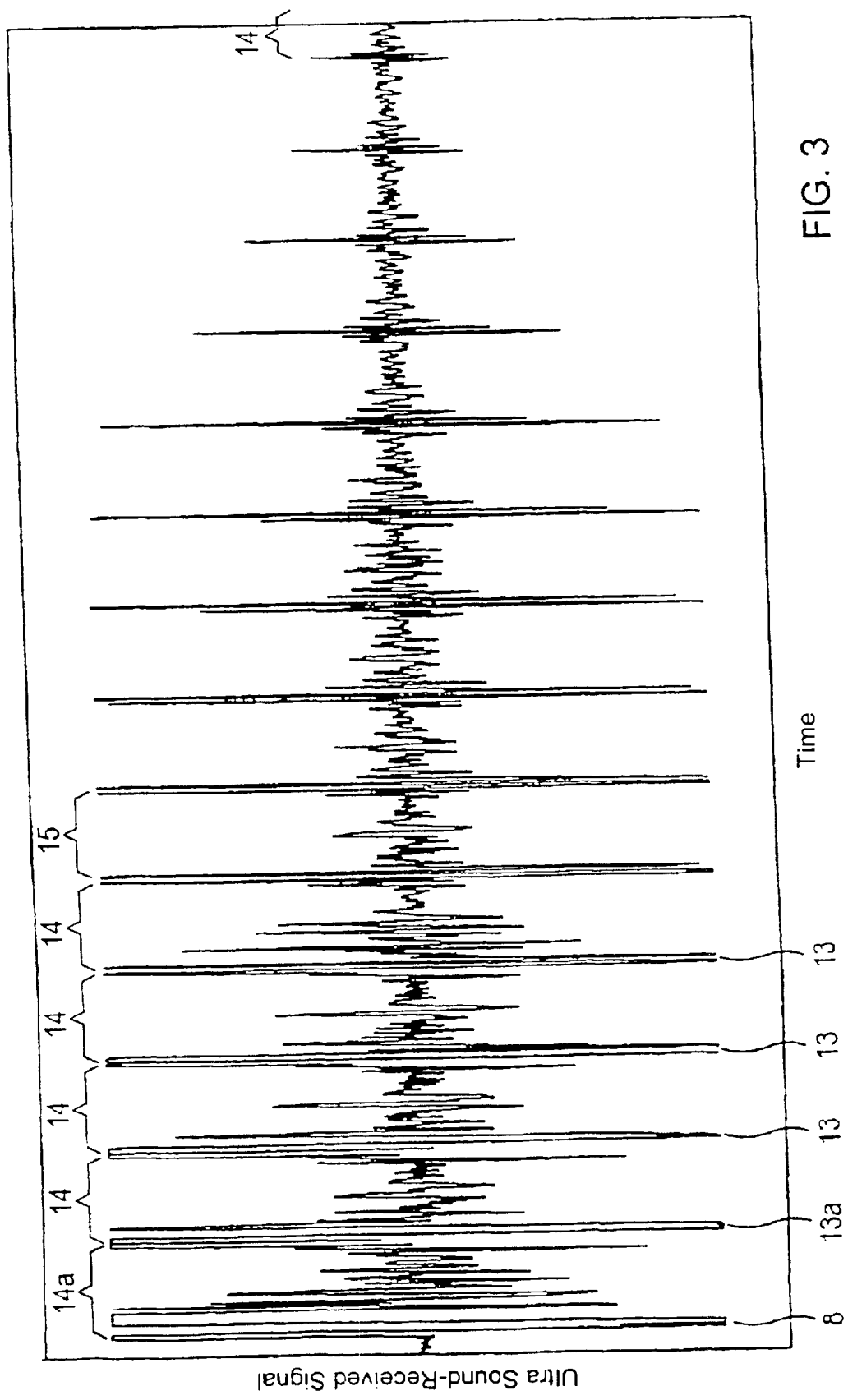
FIG. 3 is the HF image according to FIG. 2 at 100× magnification.
Figure 4:
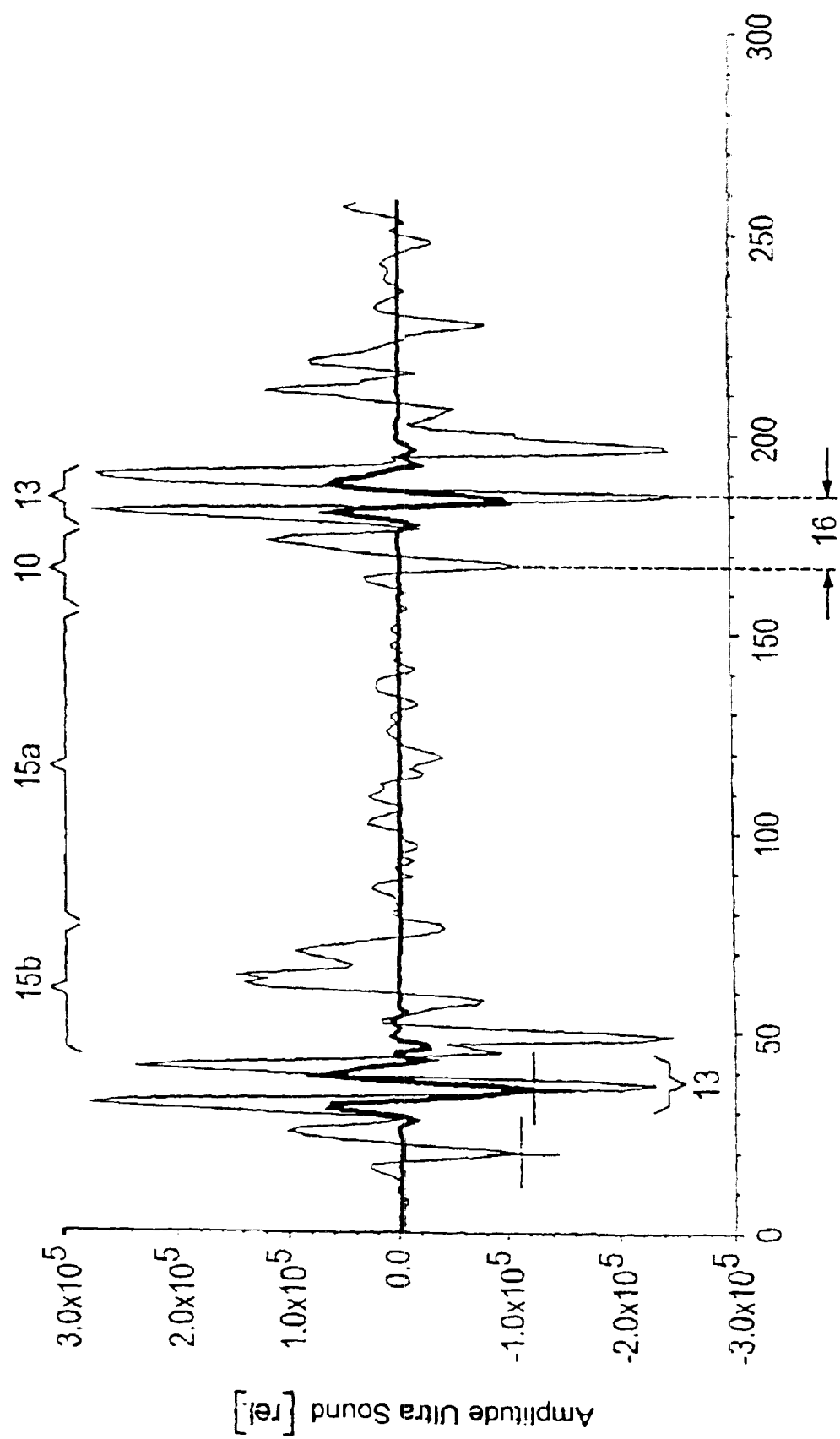
FIG. 4 is a HF image representing the result of the superposition of 14 echo periods, enlarged 1× (bold line) and 100× (thin line)
Figure 5:
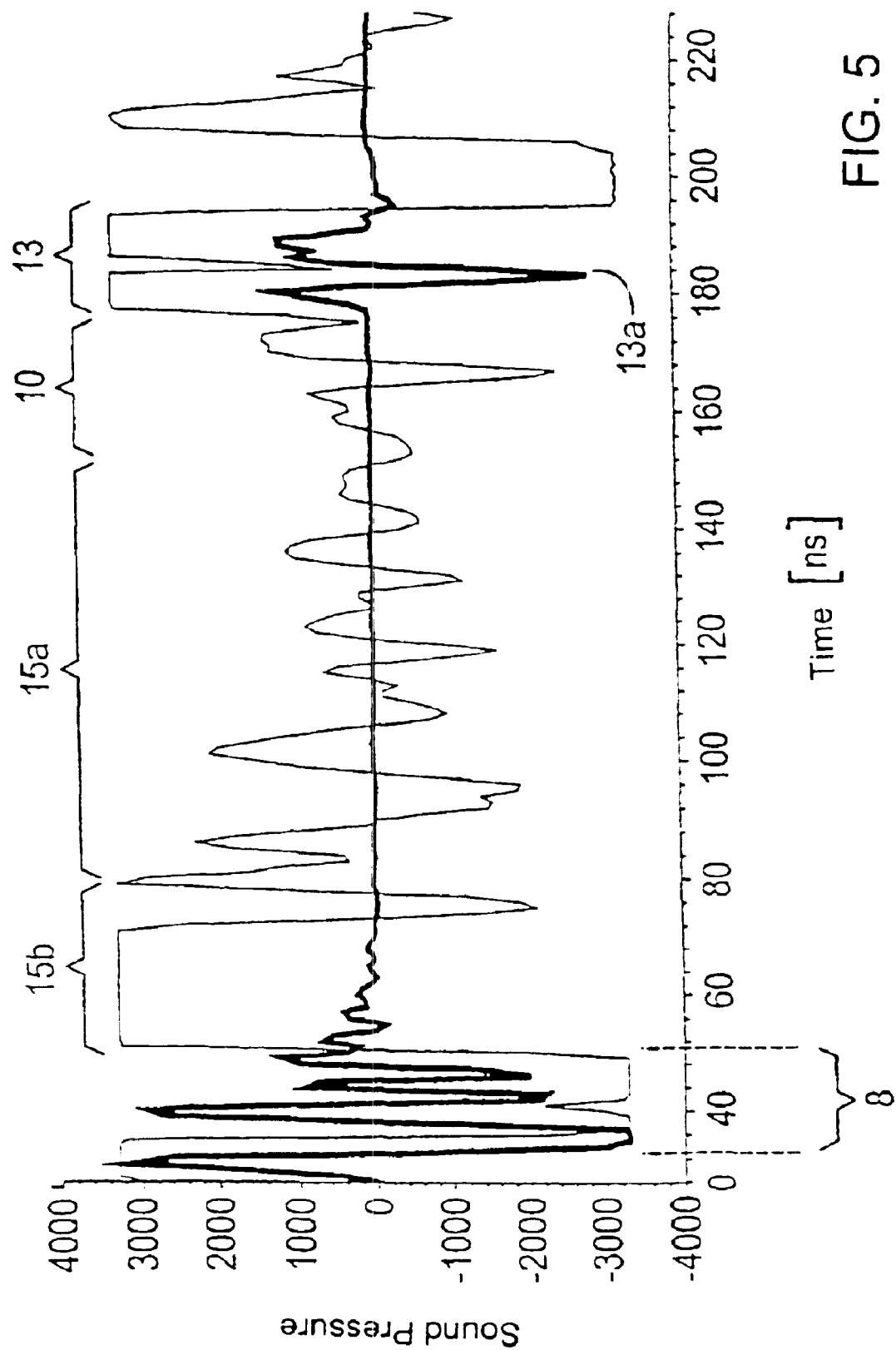
FIG. 5 is a HF image representing a first echo period, which contains a transmission impulse and a first back-wall echo, enlarged 1× (bold line) and 100× (thin line).

In order to make visible the signals between two consecutive back-wall echoes 13, i.e. the signals within an echo period 14 that is defined by the echoes, a recording with a high amplification factor such as 100× is required. Such an HF image is represented in FIG. 3. Like the HF image in FIG. 2, this is a recording not of an individual HF image but of the superposition of several HF images of several ultrasound shots. Because the ultrasound shots are identical up to inordinate electronic noise, noise signals that emerge due to imperfect damping of the ultrasound probe and due to transversal wave echoes are amplified to the same extent as the useful signals, and only the electronic noise is filtered out. For this reason, in measuring operations of the present type, i.e. the determination of sublayer thicknesses on components 1, the interface echoes 10 frequently have amplitudes in the range of the noise signal amplitudes. It is therefore difficult to identify the interface echo 10 and determine the sublayer thicknesses of the component 1. In order to remedy this problem, the HF images represented in FIG. 2 and FIG. 3, which are in digital form, are processed by the above-mentioned PC 5. With the aid of a computer program, the HF image according to FIG. 3 is resolved into its echo periods, and these are homologously superimposed. FIG. 4 represents the result of the superposition of the first 14 echo periods 14. It can be seen by comparison to FIG. 5, which represents the first echo period 14a containing the transmission impulse 8 and first back-wall echo 13a, that most of the noise signals 15a have lost intensity. This is due to the fact that the appearance of the noise signals varies in successive echo periods 14. That is, the maxima of the noise signals 15a are in different positions in the individual echo the amplitudes. Only the signal group 15b immediately following a back-wall echo 13 is closely coupled with the periodicity of the back-wall echoes, so that the signal is not damped there. But, because of its position, this signal can be excluded out of hand. The interface echo 10 is thus unambiguously detectable. In order to determine the thickness of the sublayer 7, the minimum of the interface echo 10 and the back-wall echo 12 is applied. As is generally known, the thickness of the sublayer 7 derives from the time difference between the signals. To that end, the minima of the signals can be determined, and their time difference can be converted into a layer thickness based on the known ultrasound speed.

I claim:

1. A method for ultrasound measurement of a sublayer thickness of a multilayer component with low interface reflection, which comprises the steps of:

generating a plurality of transmission impulses at a predetermined location of the multilayer component using an ultrasound probe;

digitally recording, as an HF image, resulting echo signals associated with a transmission impulse; and homologously superimposing a plurality of wall thickness echo periods of different transit times using a computer program.

2. The method according to claim 1, wherein the multilayer component is a cladding tube for nuclear fuel and the method further comprises:

determining a liner layer thickness of the cladding tube.

* * * * *